(12) United States Patent
Carroll et al.

(10) Patent No.: US 6,626,168 B1
(45) Date of Patent: Sep. 30, 2003

(54) NEBULIZING ASSEMBLY FOR INFANTS

(76) Inventors: Corey H. Carroll, 1381 S. Walnut St., Unit #2207 Anaheim, CA (US) 92802; Mary C. Carroll, 1381 S. Walnut St., Unit #2207 Anaheim, CA (US) 92802

( * ) Notice: Subject to any disclaimer, the term of this patent is extended or adjusted under 35 U.S.C. 154(b) by 153 days.

(21) Appl. No.: 09/648,134

(22) Filed: Aug. 25, 2000

(51) Int. Cl.$^7$ .............................................. A61M 11/00
(52) U.S. Cl. ........................... 128/200.14; 128/200.24; 128/206.21; 606/236
(58) Field of Search .................. 128/200.14, 200.21, 128/200.15, 206.21, 203.12, 206.27, 203.13, 203.14, 203.29; 606/234, 235, 236

(56) References Cited

U.S. PATENT DOCUMENTS

| | | | | |
|---|---|---|---|---|
| 1,395,948 A | * | 11/1921 | Drager | |
| 1,592,345 A | * | 7/1926 | Drager | |
| 3,037,501 A | | 6/1962 | Miller | |
| 3,894,537 A | * | 7/1975 | Camp | 128/203.17 |
| 3,977,432 A | * | 8/1976 | Vidal | 128/205.11 |
| D267,353 S | | 12/1982 | Sher | |
| 4,669,461 A | | 6/1987 | Battaglia et al. | |
| 4,823,784 A | * | 4/1989 | Bordoni et al. | 128/200.14 |
| 4,865,027 A | * | 9/1989 | Laanen et al. | 128/200.21 |
| 4,886,055 A | * | 12/1989 | Hoppough | 128/200.14 |
| 4,896,666 A | * | 1/1990 | Hinkle | 128/202.13 |
| 4,938,209 A | * | 7/1990 | Fry | 128/200.21 |
| 5,176,705 A | * | 1/1993 | Noble | 604/77 |
| 5,357,945 A | * | 10/1994 | Messina | 128/200.14 |
| 5,375,593 A | * | 12/1994 | Press | 128/207.18 |
| 5,462,050 A | | 10/1995 | Dahlstrand | |
| 5,586,551 A | * | 12/1996 | Hilliard | 128/200.14 |
| 5,685,291 A | | 11/1997 | Marsh | |
| 5,868,131 A | * | 2/1999 | Murchie | 128/202.13 |
| 5,904,140 A | | 5/1999 | Mcgoogan | |
| 6,138,668 A | * | 10/2000 | Patton et al. | 128/200.14 |
| 6,470,882 B1 | * | 10/2002 | Newhouse et al. | 128/200.24 |

* cited by examiner

*Primary Examiner*—Weilun Lo
*Assistant Examiner*—Mital Patel

(57) ABSTRACT

A nebulizing assembly for infants for delivering inhalable medication to infants and toddlers. The nebulizing assembly for infants includes a mask with a perimeter edge adapted to be positioned such that the user's nose and mouth are within an interior space of the mask when the perimeter edge abuts the user's face, a nipple coupled to the mask positioned to be received by the mouth of the user when the mask abuts the user's face, and a nebulizer assembly in environmental communication with the interior of the mask for delivering inhalable medication.

1 Claim, 2 Drawing Sheets

NEBULIZING ASSEMBLY FOR INFANTS

BACKGROUND OF THE INVENTION

1. Field of the Invention

The present invention relates to medication delivery devices and more particularly pertains to a new nebulizing assembly for infants for delivering inhalable medication to infants and toddlers.

2. Description of the Prior Art

The use of medication delivery devices is known in the prior art. More specifically, medication delivery devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,462,050; U.S. Pat. No. 4,669,461; U.S. Pat. No. 5,904,140; U.S. Pat. No. 5,685,291; U.S. Pat. No. 3,037,501; and U.S. Pat. No. Des. 267,353.

While these devices fulfill their respective, particular objectives and requirements, the aforementioned patents do not disclose a new nebulizing assembly for infants. The inventive device includes a mask with a perimeter edge adapted to be positioned such that the user's nose and mouth are within an interior space of the mask when the perimeter edge abuts the user's face, a nipple coupled to the mask positioned to be received by the mouth of the user when the mask abuts the user's face, and a nebulizer assembly in environmental communication with the interior of the mask for delivering inhalable medication.

In these respects, the nebulizing assembly for infants according to the present invention substantially departs from the conventional concepts and designs of the prior art, and in so doing provides an apparatus primarily developed for the purpose of delivering inhalable medication to infants and toddlers.

SUMMARY OF THE INVENTION

In view of the foregoing disadvantages inherent in the known types of medication delivery devices now present in the prior art, the present invention provides a new nebulizing assembly for infants construction wherein the same can be utilized for delivering inhalable medication to infants and toddlers.

The general purpose of the present invention, which will be described subsequently in greater detail, is to provide a new nebulizing assembly for infants apparatus and method which has many of the advantages of the medication delivery devices mentioned heretofore and many novel features that result in a new nebulizing assembly for infants which is not anticipated, rendered obvious, suggested, or even implied by any of the prior art medication delivery devices, either alone or in any combination thereof.

To attain this, the present invention generally comprises a mask with a perimeter edge adapted to be positioned such that the user's nose and mouth are within an interior space of the mask when the perimeter edge abuts the user's face, a nipple coupled to the mask positioned to be received by the mouth of the user when the mask abuts the user's face, and a nebulizer assembly in environmental communication with the interior of the mask for delivering inhalable medication.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new nebulizing assembly for infants apparatus and method which has many of the advantages of the medication delivery devices mentioned heretofore and many novel features that result in a new nebulizing assembly for infants which is not anticipated, rendered obvious, suggested, or even implied by any of the prior art medication delivery devices, either alone or in any combination thereof.

It is another object of the present invention to provide a new nebulizing assembly for infants which may be easily and efficiently manufactured and marketed.

It is a further object of the present invention to provide a new nebulizing assembly for infants which is of a durable and reliable construction.

An even further object of the present invention is to provide a new nebulizing assembly for infants which is susceptible of a low cost of manufacture with regard to both materials and labor, and which accordingly is then susceptible of low prices of sale to the consuming public, thereby making such nebulizing assembly for infants economically available to the buying public.

Still yet another object of the present invention is to provide a new nebulizing assembly for infants which provides in the apparatuses and methods of the prior art some of the advantages thereof, while simultaneously overcoming some of the disadvantages normally associated therewith.

Still another object of the present invention is to provide a new nebulizing assembly for infants for delivering inhalable medication to infants and toddlers.

Yet another object of the present invention is to provide a new nebulizing assembly for infants which includes a mask with a perimeter edge adapted to be positioned such that the user's nose and mouth are within an interior space of the mask when the perimeter edge abuts the user's face, a nipple coupled to the mask positioned to be received by the mouth of the user when the mask abuts the user's face, and a nebulizer assembly in environmental communication with the interior of the mask for delivering inhalable medication.

Still yet another object of the present invention is to provide a new nebulizing assembly for infants that provides a hands free method of administering inhalable medication to infants and toddlers.

Even still another object of the present invention is to provide a new nebulizing assembly for infants that provides comforting and reassuring stimulus to infants and toddlers.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
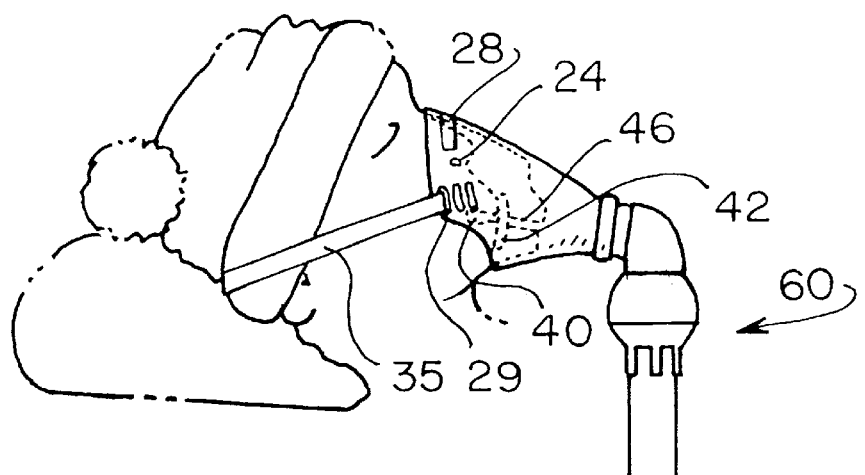
FIG. 1 is a schematic side view of a new nebulizing assembly for infants according to the present invention.
Figure 2:
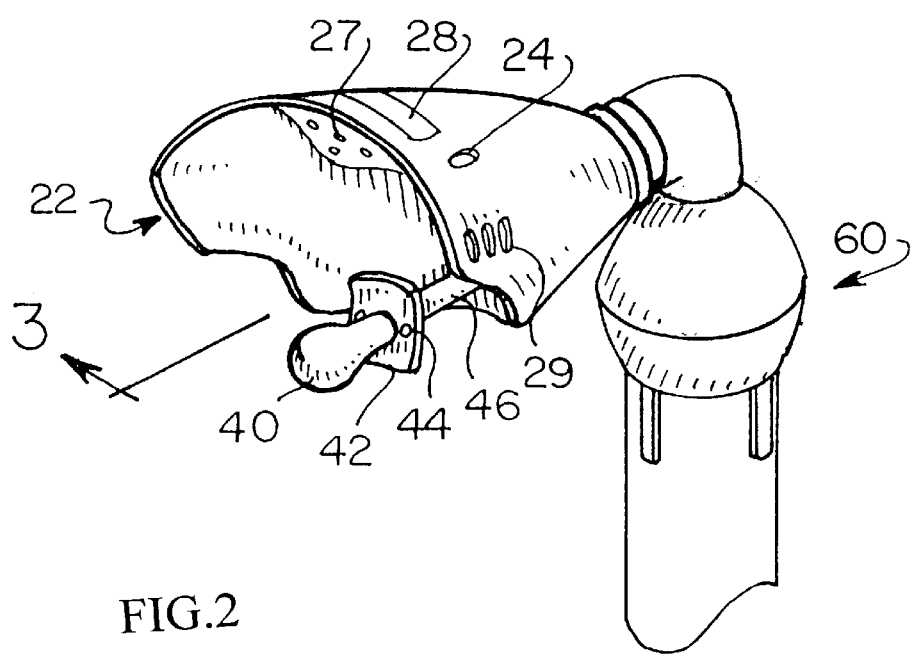
FIG. 2 is a schematic perspective view of the present invention.
Figure 3:
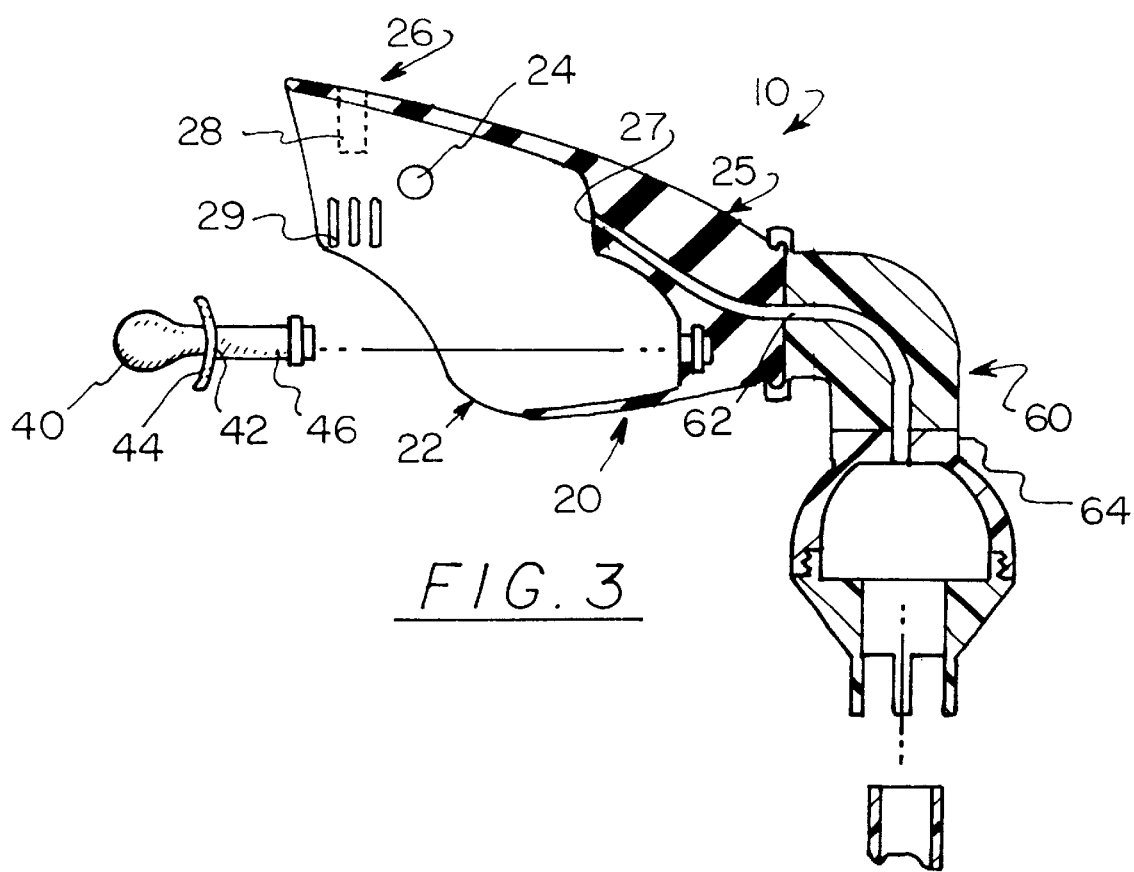
FIG. 3 is a schematic cross-section view of the present invention taken along line 3—3 of FIG. 2.

With reference now to the drawings, and in particular to FIGS. 1 through 3 thereof, a new nebulizing assembly for infants embodying the principles and concepts of the present invention and generally designated by the reference numeral 10 will be described.

As best illustrated in FIGS. 1 through 3, the nebulizing assembly for infants 10 generally comprises a mask 20, a nipple 40, and a nebulizing assembly 60 for delivering inhalable medication.

The mask 20 is constructed from a resilient flexible material. The mask 20 includes a perimeter edge 22 designed for abutting a face of a user while the mask 20 is worn such that a mouth and nose of the user are positioned within an interior space of the mask 20 when the perimeter edge 22 of the mask abuts the face of the user.

The mask 20 includes a pair of apertures 24. Thus the mask 20 is designed for permitting environmental communication between the interior of the mask 20 and ambient air surrounding the mask 20. Thus the medication mixes with the ambient air as the ambient air passes into the interior of the mask 20 for facilitating free breathing of the user while the mask 20 is worn.

The mask 20 includes a nose bridge portion 26 designed for positioning adjacent to a nose of the user while the mask 20 is being worn.

A malleable metal clip 28 is coupled to an outer surface of the nose bridge portion 26 of the mask 20. The metal clip 28 is adjustable for facilitating abutment of a portion of the perimeter edge 22 of the mask 20 proximate the nose bridge portion 26 against the face of the user.

The mask 20 is transparent for permitting visual inspection of the nose and mouth of the user while the mask 20 is being worn.

A mouth plate 42 includes a perimeter edge coupled to an interior surface of the mask 20. The mouth plate 42 is positioned for covering the mouth of the user when the mask 20 is worn.

The mouth plate 42 includes a pair of holes 44. Thus the mouth plate 42 is designed for permitting the user to breathe through the mouth of the user.

A nipple 40 extends from the mouth plate 42. The nipple 40 is positioned for being received in the mouth of the user when the mask 20 is positioned against the face of the user.

A bracing member 46 extends between an interior wall of the mask 20 and an inwardly facing surface of the mouth plate 42 for facilitating holding of the mask 20 by the mouth of the user when the nipple 40 is positioned in the mouth of the user.

A plurality of slots 29 is positioned in the outer perimeter of the mask 20. The slots 29 are designed for coupling a resilient strap 35 to the mask 20 for facilitating securement of the mask 20 to the user.

The mask 20 includes a nose portion 25. The mask includes an aperture 27 positioned at a base of the nose portion 25.

The nebulizing assembly 60 is in environmental communication with the interior of the mask 20 for delivering the inhalable medication to the interior of the mask 20 for facilitating inhalation of the medication by the user when the perimeter edge 22 of the mask 20 abuts the face of the user.

The nebulizing assembly 60 includes a connection tube member 62 with a first open end coupled to the aperture 27 at the base of the nose portion 25 of the mask 20. The nebulizing assembly 60 includes a nebulizer 64 with a cylindrical open top end.

The connection tube member 62 has a second open end. The open top end of the nebulizer 64 is insertable into the second open end of the connection tube 62.

An interior wall of the second open end tapers approaching a medial portion of the connection tube 62. Thus the interior wall of the second open end frictionally engages the open top end of the nebulizer 64.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A nebulizer assembly comprising:

a mask constructed from a resilient flexible material, said mask having a perimeter edge adapted for abutting a face of a user while the mask is worn such that a mouth and nose of the user are positioned within an interior space of said mask when said perimeter edge of said mask abuts the face of the user;

a nebutizing assembly in environmental communication with said interior of said mask for delivering inhalable medication to said interior of said mask for facilitating inhalation of the medication by the user when said perimeter edge of said mask abuts the face of the user;

said mask having a pair of apertures whereby said mask is adapted for permitting environmental communication between said interior of said mask and ambient air surrounding said mask whereby the medication mixes with the ambient air as the ambient air passes into said interior of said mask for facilitating free breathing of the user while the mask is worn;

said mask including a nose bridge portion adapted for positioning adjacent to a nose of the user while the mask is being worn;

a malleable metal clip coupled to an outer surface of said nose bridge portion of said mask, said metal clip being adjustable for facilitating abutment of a portion of said perimeter edge of said mask proximate said nose bridge portion against the face of the user;

said mask being transparent for permitting visual inspection of the nose and mouth of the user while the mask is being worn;

a mouth plate mounted on an interior surface of said mask, said mouth plate having a perimeter edge located opposite of said mask said mouth plate being positioned for covering the mouth of the user when the mask is worn;

said mouth plate having a pair of holes whereby said mouth plate is adapted for permitting the user to breathe through the mouth of the user;

a nipple extending from said mouth plate, said nipple being positioned for being received in the mouth of the user when the mask is positioned against the face of the user;

a bracing member extending between an interior wall of said mask and an inwardly facing surface of said mouth plate for facilitating holding of said mask by the mouth of the user when the nipple is positioned in the mouth of the user;

a plurality of slots positioned in said outer perimeter of said mask, said slots being adapted for coupling a resilient strap to said mask for facilitating securement of said mask to the user;

said mask including a nose portion adapted for positioning adjacent the nose of the user;

said mask including an aperture positioned at a base of said nose portion;

said nebulizing assembly including a connection tube member having a first open end coupled to said aperture at said base of said nose portion of said mask;

said nebulizing assembly including a nebulizer having a cylindrical open top end;

said connection tube member having a second open end, said open top end of said nebulizer being insertable into said second open end of said connection tube; and an interior wall of said second open end tapering approaching a medial portion of said connection tube whereby said interior wall of said second open end frictionally engages said open top end of said nebulizer.

* * * * *